United States Patent [19]
Polymeropoulos et al.

[11] Patent Number: 5,468,610
[45] Date of Patent: Nov. 21, 1995

[54] THREE HIGHLY INFORMATIVE MICROSATELLITE REPEAT POLYMORPHIC DNA MARKERS

[75] Inventors: Mihael H. Polymeropoulos, Bethesda; Carl R. Merril, Rockville, both of Md.

[73] Assignee: The Government of the United States of America as represented by the Secretary of the Department of Health and Human Services, Washington, D.C.

[21] Appl. No.: 74,275

[22] Filed: Jun. 9, 1993

Related U.S. Application Data

[63] Continuation of Ser. No. 707,501, May 29, 1991, abandoned.

[51] Int. Cl.$^6$ ............... C12Q 1/68; C12P 19/34; C07H 21/04
[52] U.S. Cl. ............... 435/6; 435/91.2; 935/78; 536/24.33; 536/24.31
[58] Field of Search ............ 435/6, 91.2; 536/24.33

[56] References Cited

U.S. PATENT DOCUMENTS

| | | | |
|---|---|---|---|
| 4,683,195 | 7/1987 | Mullis et al. | 435/91.2 |
| 4,683,202 | 7/1987 | Mullis | 435/91.2 |
| 4,800,159 | 1/1989 | Mullis et al. | 435/91 |
| 4,897,214 | 1/1990 | Gazzani | 435/6 |
| 5,001,050 | 3/1991 | Blanco et al. | 435/6 |

OTHER PUBLICATIONS

Polymeropoulos et al. (Feb. 11, 1991) Nucleic Acids Res., vol. 19(3), p. 689.
Weber et al "Abundant Class of Human DNA Polymorphisms Which Can Be Typed Using the Polymerase Chain Reaction", pp. 388–396, Am. J. Hum. Genet 44, 1989.
Tautz et al, Nucleic Acids Research, vol. 12, No. 10, "Simple Sequences Are Ubiquitous Repetitive Components of Eukaryotic Genomes", pp. 4127–4138, 1984.
Nakamura et al, "Variable Number of Tandem Repeat (VNTR) Markers for Human Gene Mapping", Science vol. 235 pp. 1616–1622, 1987.
Overhauser et al, Nucleic Acids Research, vol. 15, No. 11, "Identification of 28 DNA Fragments That Detect RFLPs in 13 Distinct Physical Regions of the Short Arm of Chromosome 5", pp. 4617–4627, 1987.
Jeffreys et al, "Hypervariable 'minisatellite' Regions in Human DNA", vol. 314, pp. 67–73, 1985.
Weber et al, "Dinucleotide Repeat Polymorphism at the D10S89 Locus", Nucleic Acids Research, vol. 18, No. 15, p. 4637.
Dariavach et al. (1988) European Journal of Immunology, vol. 18, pp. 1901–1905.
Moos et al. (1983) The EMBO Journal, vol. 2(5), pp. 757–761.
Chen et al. (1989) Genomics, vol. 4, pp. 479–497.

*Primary Examiner*—W. Gary Jones
*Assistant Examiner*—Lisa Arthur
*Attorney, Agent, or Firm*—Lowe, Price, LeBlanc & Becker

[57] ABSTRACT

The invention relates to polymorphic markers (two tetranucleotide and one dinucleotide repeat polymorphisms) that are useful for human individualization. Applications are in forensic medicine and for paternity and prenatal screening as well as genetic mapping. These markers are characterized by sets of oligonucleotide primers according to the invention useful in PCR amplification and DNA segment resolution. The invention further relates to an assay for measuring the subtle differences in genetic material regarding an added or omitted set of dinucleotide or tetranucleotide repeat polymorphisms which comprises obtaining an amount of nucleotide segments effective for testing, amplifying the segments by the PCR procedure using at least one primer nucleotide sequence according to the present invention, resolving the amplified segments using gel electrophoresis, and comparing the resolved segments by autoradiography to observe the differences in migration patterns due to structural differences. The assay according to the invention is easy to perform and results can be obtained within 24 hours. It is not uncommon for results to be available within 3–4 hours. Accordingly, the invention also relates to an improved PCR procedure and a PCR assay kit which comprise nucleotides according to the invention.

12 Claims, 2 Drawing Sheets

FIGURE 1

AATCTGGGCG ACAAGAGTGA　　　　　　20

FIGURE 2

ACATCTCCCC TACCGCTATA　　　　　　20

FIGURE 3

TCCAGCCTCG GAGACAGAAT　　　　　　20

FIGURE 4

AGTCCTTTCT CCAGAGCAGG T　　　　　21

FIGURE 5

GCCAGTGATG CTAAAGGTTG　　　　　　20

FIGURE 6

AACATACGTG GCTCTATGCA　　　　　　20

FIGURE 7

| | | | | | |
|---|---|---|---|---|---|
| AATCTGGGCG | ACAAGAGTGA | AACTCCGTCA | AAAGAAAGAA | AGAAAGAGAC | 50 |
| AAAGAGAGTT | AGAAAGAAAG | AAAGAGAGAG | AGAGAGAAAG | GAAGGAAGGA | 100 |
| AGAAAAAGAA | AGAAAAAGAA | AGAAAGAGAA | AGAAAGAAAG | AGAAAGAAAG | 150 |
| AAAGAAAGAA | AGAAAGAAAG | AAAGAAAGAA | AGAAAGAAAA | AGAAAGAAAG | 200 |
| AAAGAAAGAA | AGAAAGAAAG | AAAGAAAGAA | AGAAAGAAAG | AAAGAAAGGA | 250 |
| AGGAAAGAAA | GAGCAAGTTA | CTATAGCGGT | AGGGGAGATG | T | 291 |

FIGURE 8

| | | | | | |
|---|---|---|---|---|---|
| GCCAGTGATG | CTAAAGGTTG | TATTGCATAT | ATACATATAT | ATATATATAT | 50 |
| ATATATATAT | ATATATATAT | ATATATATAT | ATATATATAT | TTTAATTTGA | 100 |
| TAGTATTGTG | CATAGAGCCA | CGTATGTT | | | 128 |

FIGURE 9

| | | | | | |
|---|---|---|---|---|---|
| TCCAGCCTCG | GAGACAGAAT | GAGACTCCAT | CAAAAACAAG | AAAGAAAGAA | 50 |
| AGACAAAGAG | AGAAAGAAAG | AAAGAAAGAA | AGAAAGAAAG | AGAGAGAGAG | 100 |
| AGAGAGAGAG | AGAAAGAAAG | AAAGAAAGAA | AGAAAGAAAG | AAAGAAAGAA | 150 |
| AGAAAGAAAG | AAAGAAAGAA | GGAAAGAAAG | AAAGGAAACT | AAAATAACTA | 200 |
| AATAACTGAG | TAGCACCACA | CCACCTGCTC | TGGAGAAAGG | ACT | 243 |

THREE HIGHLY INFORMATIVE MICROSATELLITE REPEAT POLYMORPHIC DNA MARKERS

This application is a continuation of application Ser. No. 07/707,501 now abandoned filed May 29, 1991.

TECHNICAL FIELD

This application relates to genetic testing with polymorphic DNA markers having repeat sequences to provide a rapid and convenient high resolution process for distinguishing target nucleic acid segments on the basis of nucleotide differences according to human individualization wherein the nucleic acid segments differ in size.

BACKGROUND ART

The science of genetics has taken a keen interest in the identification of human individualization and genetic relationships between individuals. Each individual has hereditary material (DNA, "nucleotides") which is unique to that individual and hereditary material which is related to that of others. Procedures have been developed which are based on identification and characterization of changes in DNAs, which are changes in DNA (DNA polymorphisms) due to nucleotide substitution, insertion, or deletion within the chains of DNAs.

In the field of forensic medicine, for example, there is a keen interest in such polymorphisms for identification purposes. Forensic geneticist have developed many techniques to compare homologous segments of DNA to determine if the segments are identical or if they differ in one or more nucleotides. Practical applications of these techniques relate to fields other than forensic medicine, for example, genetic disease diagnosis and human genome mapping.

At the present time in this art, the most accurate and informative way to compare DNA segments requires a method which provides the complete nucleotide sequence for each DNA segment. Particular techniques have been developed for determining actual sequences in order to study mutation in human genes. See, for example, Proc. Natl. Acad. Sci. U.S.A. 85, 544–548 (1988) and Nature 330, 384–386 (1987). However, because of the extensive amounts of time and high costs to determine, interpret, and compare sequence information, presently it is not practical to use extensive sequencing for compare more than just a few DNA segments.

In genetic mapping, the most frequently used screening for DNA polymorphisms arising from mutations consist of digesting the DNA strand with restriction endonucleases and analyzing the resulting fragments by means of Southern blots. See Am. J. Hum. Genet. 32, 314–331 (1980) or Sci. Am. 258, 40–48 (1988). Since mutations often occur randomly they may affect the recognition sequence of the endonuclease and preclude the enzymatic cleavage at that cite. Restriction fragment length polymorphism mappings (RFLPS) are based on changes at the restriction site. They are accurate but not very informative (PIC [0.3). The major problem with RFLPs is the inability of a test to detect changes that do not affect cleavage with a restriction endonuclease. As in many of the test methods in the DNA art, the methods used to detect RFLPs are very labor intensive and expensive, especially the techniques which includes Southern blot analysis.

Another technique for detecting specific mutations in particular DNA segment involves hybridizing DNA segments which are being analyzed (target DNA) with a complimentary, labeled oligonucleotide probe. See Nucl. Acids Res. 9, 879–894 (1981). Since DNA duplexes containing even a single base pair mismatch exhibit high thermal instability, the differential melting temperature can be used to distinguish target DNAs that are perfectly complimentary to the probe from target DNAs that only differ by a single nucleotide. This method has been adapted to detect the presence or absence of a specific restriction site, U.S. Pat. No. 4,683,194. The method involves using an end-labeled oligonucleotide probe spanning a restriction site which is hybridized to a target DNA. The hybridized duplex of DNA is then incubated with the restriction enzyme appropriate for that site. Reformed restriction sites will be cleaved by digestion in the pair of duplexes between the probe and target by using the restriction endonuclease. The specific restriction site is present in the target DNA if shortened probe molecules are detected.

Another process for studying differences in DNA structure is the primer extension process which consists of hybridizing a labeled oligonucleotide primer to a template RNA or DNA and then using a DNA polymerase and deoxynucleoside triphosphates to extend the primer to the 5' end of the template. Resolution of the labeled primer extension product is then done by fractionating on the basis of size, e.g., by electrophoresis via a denaturing polyacrylamide gel. This process is often used to compare homologous DNA segments and to detect differences due to nucleotide insertion or deletion. Differences due to nucleotide substitution are not detected since size is the sole criterion used to characterize the primer extension product.

Another process exploits the fact that the incorporation of some nucleotide analogs into DNA causes an incremental shift of mobility when the DNA is subjected to a size fractionation process, such as electrophoresis. Nucleotide analogs can be used to identify changes since they can cause an electrophoretic mobility shift. See, U.S. Pat. No. 4,879,214.

Unfortunately, the above techniques used for identification of polymorphisms are either not very informative or take a long period of time to perform. For example, techniques which identify changes in individual nucleotides on a particular DNA strand often take at least three to four days to perform. Accordingly, such tests are very labor intensive and expensive to perform.

Further, subtle genetic differences among related individuals regarding nucleotides which are substituted in the DNA chains are difficult to detect. VNTR's or Jeffrey's probes (which the FBI is using to test and identify DNA chains) are very informative but labor intensive, in distinction to microsatellites as our which are equally informative PCR based polymormismic.

The use of certain nucleotide repeat polymorphisms for identifying or comparing DNA segments have been described by Weber & May 89 Am Hum Genet 44:388, Litt & Luthy '89 Am) Hum Genet 44:397). However the particular polymorphism genetic segments and primers used to identify the polymorphisms (for identification and comparison purposes) of the present invention have not been previously known or suspected.

Accordingly, there a need in this art for a rapid, simple, inexpensive and accurate technique having a very high resolution value to determine relationships between individuals and differences in degree of relationships. Also, there is a need in the art for a very accurate genetic relationship test procedure which uses very small amounts of an original DNA sample, yet produces very accurate results. This is particularly true in the forensic medicine area and criminology, since often times very small samples of DNA are available for testing.

DISCLOSURE OF THE INVENTION

An object of the present invention is to provide a fast and accurate test for measuring the subtle differences in individuals by way of genetic testing.

Another object of the invention relates to polymorphic markers (two tetranucleotide and one dinucleotide repeat polymorphisms) that can be used for human individualization.

A further object of the invention is to provide a fast and accurate technique for measuring the subtle differences in individuals by way of genetic testing that can be applied in multiple areas, e.g., forensic screening, paternity and prenatal screening and genetic mapping.

A still further object is to provide an improved method for conducting a PCR procedure using an effective amount of a nucleotide according to the present invention and to provide an PCR assay kit comprising an effective amount of a nucleotide according to the present invention and ancillary PCR reagents.

BRIEF DESCRIPTION OF DRAWINGS

FIG. 1 relates to a nucleotide sequence according to SEQ ID NO:1.

FIG. 2 relates to a nucleotide sequence according to SEQ ID NO:2.

FIG. 3 relates to a nucleotide sequence according to SEQ ID NO:3.

FIG. 4 relates to a nucleotide sequence according to SEQ ID NO:4.

FIG. 5 relates to a nucleotide sequence according to SEQ ID NO:5.

FIG. 6 relates to a nucleotide sequence according to SEQ ID NO:6.

FIG. 7 relates to a nucleotide sequence according to SEQ ID NO: 7.

FIG. 8 relates to a nucleotide sequence according to SEQ ID NO:8.

FIG. 9 relates to a nucleotide sequence according to SEQ ID NO:9.

BEST MODE FOR CARRYING OUT THE INVENTION

The present invention provides a fast and accurate test for measuring subtle genetic differences in individuals by way of genetic testing. The invention further relates to polymorphic markers (two tetranucleotide and one dinucleotide repeat polymorphisms) that can be used for human individualization. Applications for the technique and markers according to the invention are for example, in forensic screening, in paternity and prenatal screening as well as in genetic mapping.

The invention relates to polymorphic markers (two tetranucleotide and one dinucleotide repeat polymorphisms) that are useful for human individualization of forensic screen, and for paternity and prenatal screening as well as genetic mapping. The markers according to the present invention have high polymorphism information content (PIC) values. These markers are characterized by sets of oligonucleotide primers as follows:

1. Set 1, PIC 0.92
   a. A nucleotide sequence according to SEQ ID NO:1
   b. A nucleotide sequence according to SEQ ID NO:2
2. Set 2, PIC 0.91
   a. A nucleotide sequence according to SEQ ID NO:3
   b. A nucleotide sequence according to SEQ ID NO:4
3. Set 3, PIC 0.92
   a. A nucleotide sequence according to SEQ ID NO:5
   b. A nucleotide sequence according to SEQ ID NO:6.

These polymorphic markers (two tetranucleotide and one dinucleotide repeat polymorphisms which are also accompanied by beginning and ending nucleotide sequences) that can be used for human individualization are further characterized by the following marker sequences.

1. A nucleotide sequence having a repeat polymorphism according to SEQ ID NO:7.
2. A nucleotide sequence having a repeat polymorphism according to SEQ ID NO:8.
3. A nucleotide sequence having a repeat polymorphism according to SEQ ID NO:9.

Since a polymorphic marker and an index locus occur as a "pair", attaching a primer oligonucleotide according to the present invention to the polymorphic marker allows PCR amplification of the segment pair. The amplified DNA segment can then be resolved by electrophoresis and autoradiography. A resulting autoradiography can then be analyzed for its similarity to another DNA segment autoradiography. Following the PCR amplification procedure, electrophoretic motility enhancing DNA analogs may optionally be used to increase the accuracy of the electrophoresis step.

Also, the invention relates to a method for conducting a PCR procedure comprising using an effective amount of at least one nucleotide according to according to the invention as set forth above, wherein the nucleotide is part of a primer pair of nucleotides selected from the group of nucleotide pairs consisting of a) a nucleotide sequence having the sequence as set forth in SEQ ID NO:1 and a nucleotide sequence as set forth in SEQ ID NO:2;

b) a nucleotide sequence having the sequence as set forth in SEQ ID NO:3 and a nucleotide sequence as set forth in SEQ ID NO:4; and c) a nucleotide sequence having the sequence as set forth in SEQ ID NO:5 and a nucleotide sequence as set forth in SEQ ID NO:6.

Therefore, the invention further relates to an assay for measuring the subtle differences in genetic material regarding an added or omitted set of dinucleotide or tetranucleotide repeat polymorphisms selected from the group consisting of a sequence according to SEQ ID NO:7, a sequence according to SEQ ID NO:8 and a sequence according to SEQ ID NO:9, which comprises a. obtaining nucleotide segments comprising said repeat polymorphisms in an amount effective for testing, b. amplifying said segments by a PCR procedure using a pair of oligonucleotide primers capable of amplifying said polymorphism containing segments, c. resolving the amplified segments using page gels electrophoresis, and d. comparing the resolved segments by autoradiography to observe the differences in migration patterns due to length variation.

Preferably, the invention further relates to an assay for measuring the subtle differences in genetic material regarding an added or omitted set of dinucleotide or tetranucleotide repeat polymorphisms selected from the group consisting of a sequence according to SEQ ID NO:7, a sequence according to SEQ ID NO:8 and a sequence according to SEQ ID NO:9, which comprises a. obtaining nucleotide segments comprising said repeat polymorphisms in an amount effective for testing, b. amplifying said segments by a PCR procedure using the pair of oligonucleotide primers selected from the group consisting of a sequence according to SEQ ID NO:1, a sequence according to SEQ ID NO:2, a sequence according to SEQ ID NO:3, a sequence according to SEQ ID NO:4, a sequence according to SEQ ID NO:5, or a sequence according to SEQ ID NO:6, c. resolving the amplified segments using page gels electrophoresis, and d. comparing the resolved segments by autoradiography to observe the differences in migration patterns due to length variation.

Still further, the invention relates to an assay kit for conducting a PCR procedure comprising an effective amount of at least one nucleotide having a sequence according to the invention as set forth above, wherein the nucleotide is part of a primer pair of nucleotides selected from the group of nucleotide pairs consisting of a) a nucleotide sequence having the sequence as set forth in SEQ ID NO:1 and a nucleotide sequence as set forth in SEQ ID NO:2;

b) a nucleotide sequence having the sequence as set forth in SEQ ID NO:3 and a nucleotide sequence as set forth in SEQ ID NO:4; and c) a nucleotide sequence having the sequence as set forth in SEQ ID NO:5 and a nucleotide sequence as set forth in SEQ ID NO:6, in combination with an effective amount of ancillary PCR reagents.

Accordingly, the above described polymorphisms are useful for human sample individualization, because of their high PIC values. Since the described polymorphic systems are based on the polymerase chain reaction (PCR), only minute (40 nanograms) amounts of genomic DNA are required for each test. The target sequences range from 92 to 310 base pairs so that high molecular weight DNA is not necessary, and common problems such as shearing of DNA will have minimal impact on the performance of the assay. The assay is easy to perform and results can be obtained within 24 hours. It is not uncommon for results to be available within 3–4 hours. By comparison, the prior art methods require a number of days before results are available, usually 3–4 days are required.

Further, the assay according to the invention is able to detect very small differences in nucleotide sequences. A single omission or addition of the repeat sequence will change the mobility due to the electrical nature and molecular weight of the target nucleotide sequence. These differences are clearly visible on the autoradiographs after electrophoresis.

Microsatellite repeat polymorphisms have been shown to be useful tools in DNA analysis. The three polymorphisms described here are original and are based on previously sequenced genes. The two tetranucleotide repeat markers described, can be scored easily since allele sizes differ by four base pairs. The most commonly used technique used in forensic screening is based on minisatellite markers, in distinction to the PCR able microsatellites described in the present invention.

The general PCR technique step is conducted generally as described in U.S. Pat. No. 4,683,195 to Mullis et al and U.S. Pat. No. 4,683,202 to Mullis et al, which are hereby incorporated by reference thereto. Further, electrical motility enhancing DNA analogs can optionally be used during the replication and amplification PCR procedure.

The degree of polymorphism in the genetic segments according to the present invention, which polymorphisms yield highly informative identification test results, is surprising and unexpected. The high PIC value (approximately 0.9) is totally unexpected.

Accordingly, the use of a PCR procedure and PCR primers pairs, such as those primer sequences according to SEQ ID NO:1 to SEQ ID NO:6, to detect the polymorphism DNA segment according to the present invention yields excellent results. Such results are sufficiently accurate and informative to accurately identify DNA segments and determine degrees of relationship between DNA segments of individuals.

Moreover, conducting three sets of PCR procedures on the same DNA segment samples while using a different PCR primer pair according to the present invention for each of the three procedures yields extraordinarily accurate and informative test results. Comparison of the three sets of test results data provides extremely accurate DNA segment identification.

The following examples are provided to more specifically describe the invention which is not limited to the following examples.

The described oligonucleotide primers are used to amplify the target sequences using PCR, under the following conditions:

Example 1

The samples are of DNA are prepared as follows.

60 ng of genomic DNA are used as template for PCR with 80 ng of each oligonucleotide primer, 0.6 units of Taq Polymerase 50 mM KCL, 10 mM Tris (pH 8.3), 1.5 mM $MgCl_2$, 0.01% gelatin, 200 uM of each dGTP, dATP, dTTP, 2.5 uM dCTP and 10 microcuries of alpha P32 dCTP., in a final reaction volume of 15 microliters. The samples are overlayed with 15 microliters of mineral oil to prevent evaporation.

EXAMPLE 2

PCR is performed for each of the samples and primers described in Example 1, above.

PCR is performed in a Techne MW-1 microplate thermocycler under the following conditions denaturation of 94 degrees C for 1.4 min., annealing at 55 degrees C. for 2 min., and extension at 72 degrees C. for 2 min. The cycle is repeated 30 times with a final extension at 72 degrees C for 10 min.

EXAMPLE 3

The amplified DNA segments from each of the samples described in Example 2 above are resolved by electrophoresis as follows.

Two microliters of each PCR reaction mixture sample are electrophoresed on a 6% PAGE sequencing gel and visualized by autoradiography. Exposure times for the autoradiography range from 3–16 hours.

We claim:

1. A DNA fragment consisting of a nucleotide sequence selected from the group consisting of a sequence according to SEQ ID NO:1, a sequence according to SEQ ID NO:2, a sequence according to SEQ ID NO:3, a sequence according to SEQ ID NO:4, a sequence according to SEQ ID NO:5, or a sequence according to SEQ ID NO:6.

2. A DNA fragment according to claim 1, wherein the sequence is a sequence according to SEQ ID NO:1.

3. A DNA fragment according to claim 1, wherein the sequence is a sequence according to SEQ ID NO:2.

4. A DNA fragment according to claim 1, wherein the sequence is a sequence according to SEQ ID NO:3.

5. A DNA fragment according to claim 1, wherein the sequence is a sequence according to SEQ ID NO:4.

6. A DNA fragment according to claim 1, wherein the sequence is a sequence according to SEQ ID NO:5.

7. A DNA fragment according to claim 1, wherein the sequence is a sequence according to SEQ ID NO:6.

8. An assay kit for conducting a polymerase chain reaction procedure to detect an added or omitted set of dinucleotide or tetranucleotide repeat polymorphisms, wherein said assay results in a polymorphic information content of about 0.9 comprising an effective amount for amplification by polymerase chain reaction of a pair of oligonucleotide primers selected from the group consisting of a) a sequence as set forth in SEQ ID NO:1 and a sequence as set forth in SEQ ID NO:2;

b) a sequence as set forth in SEQ ID NO:3 and a sequence as set forth in SEQ ID NO:4; and c) a sequence as set forth in SEQ ID NO:5 and a sequence as set forth in SEQ ID NO:6, in combination with an effective amount of ancillary polymerase chain reaction reagents.

9. A method for conducting a polymerase chain reaction procedure to detect an added or omitted set of dinucleotide or tetranucleotide repeat polymorphisms, wherein said method results in a polymorphic information content of about 0.9 comprising a) obtaining a DNA fragment comprising said repeat polymorphisms in an amount sufficient for amplification by polymerase chain reaction, b) amplifying the repeat polymorphisms by polymerase chain reaction using a pair of oligonucleotide primers selected from the group consisting of (1) a primer having the sequence of SEQ ID NO:1 and a primer having the sequence of SEQ ID NO:2; (2) a primer having the sequence of SEQ ID NO:3 and a primer substantially having the sequence of SEQ ID NO:4; and (3) a primer substantially having the sequence of SEQ ID NO:5 and a primer having the sequence of SEQ ID NO:6;

c) determining the length of the amplification product containing the repeat polymorphisms of step (b) in order to detect genetic differences which result from added or omitted sets of dinucleotide or tetranucleotide repeat polymorphisms.

10. An assay for measuring differences in genetic material to detect an added or omitted set of dinucleotide or tetranucleotide repeat polymorphisms in forensic screening, paternity, prenatal screening, or genetic mapping, wherein said assay results in a polymorphic information content of about 0.9, and wherein said genetic material comprises a DNA fragment comprising a nucleotide sequence selected from the group consisting of a sequence according to SEQ ID NO: 7, a sequence according to SEQ ID NO:8 and a sequence according to SEQ ID NO:9, which assay comprises a) obtaining a DNA fragment comprising repeat polymorphisms comprising a nucleotide sequence selected from the group consisting of a sequence according to SEQ ID NO:7, a sequence according to SEQ ID NO: 8 and a sequence substantially according to SEQ ID NO:9 in an amount sufficient for amplification by polymerase chain reaction, b) amplifying the repeat polymorphisms by polymerase chain reaction using a pair of oligonucleotide primers capable of detecting said repeat polymorphism selected from the group consisting of (1) a primer having the sequence of SEQ ID NO:1 and a primer having the sequence of SEQ ID NO:2; (2) a primer having the sequence of SEQ ID NO:3 and a primer having the sequence of SEQ ID NO:4; and (3) a primer having the sequence of SEQ ID NO:5 and a primer having the sequence of SEQ ID NO:6;

(c) determining the length of the amplification product containing the repeat polymorphisms of step (b) in order to detect genetic differences which result from added or omitted sets of dinucleotide or tetranucleotide repeat polymorphisms.

11. A method for detecting differences in genetic material in (a) an added or omitted set of (AT)n polymorphisms in the human CTLA-4 gene, (b) a (GAAA)n polymorphism in the human growth hormone loci, or (c) a G(AAA)n polymorphism in the human cytoplasmic betaactin related pseudogene, wherein said method results in a polymorphic information content of about 0.9, which method comprises a) obtaining a DNA fragment comprising repeat polymorphisms in an amount sufficient for amplification by polymerase chain reaction, b) amplifying the DNA fragment by polymerase chain reaction using a pair of oligonucleotide primers capable of detecting said polymorphisms selected from the group consisting of (1) a primer having the sequence of SEQ ID NO:1 and a primer having the sequence of SEQ ID NO:2; (2) a primer having the sequence of SEQ ID NO:3 and a primer having the sequence of SEQ ID NO:4; and (3) a primer having the sequence of SEQ ID NO:5 and a primer having the sequence of SEQ ID NO:6;

(c) performing a polymerase chain reaction using a primer pair from step (b) to produce amplification products; and (d) detecting the length of the amplification product of step (c) in order to detect genetic differences which result from added or omitted sets of dinucleotide or tetranucleotide repeat polymorphisms.

12. An oligonucleotide primer consisting of a nucleotide sequence selected from the group consisting of SEQ ID NO:1, SEQ ID NO:2, SEQ ID NO:3, SEQ ID NO:4, SEQ ID NO:5 and SEQ ID NO:6.

* * * * *

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

AATCTGGGCG ACAAGAGTGA        20

( 2 ) INFORMATION FOR SEQ ID NO:2:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

ACATCTCCCC TACCGCTATA        20

( 2 ) INFORMATION FOR SEQ ID NO:3:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

TCCAGCCTCG GAGACAGAAT        20

( 2 ) INFORMATION FOR SEQ ID NO:4:

( i ) SEQUENCE CHARACTERISTICS:
        ( A ) LENGTH: 21
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

AGTCCTTTCT CCAGAGCAGG T        21

( 2 ) INFORMATION FOR SEQ ID NO:5:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

GCCAGTGATG CTAAAGGTTG                                                                    20

( 2 ) INFORMATION FOR SEQ ID NO:6:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

AACATACGTG GCTCTATGCA                                                                    20

( 2 ) INFORMATION FOR SEQ ID NO:7:

( i ) SEQUENCE CHARACTERISTICS:
        ( A ) LENGTH: 291
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:7:

AATCTGGGCG ACAAGAGTGA AACTCCGTCA AAAGAAAGAA AGAAAGAGAC AAAGAGAGTT        60

AGAAAGAAAG AAAGAGAGAG AGAGAGAAAG GAAGGAAGGA AGAAAAAGAA AGAAAAAGAA       120

AGAAAGAGAA AGAAAGAAAG AGAAAGAAAG AAAGAAAGAA AGAAAGAAAG AAAGAAAGAA       180

AGAAAGAAAA AGAAAGAAAG AAAGAAAGAA AGAAAGAAAG AAAGAAAGAA AGAAAGAAAG       240

AAAGAAAGGA AGGAAAGAAA GAGCAAGTTA CTATAGCGGT AGGGGAGATG T                291

( 2 ) INFORMATION FOR SEQ ID NO:8:

( i ) SEQUENCE CHARACTERISTICS:
        ( A ) LENGTH: 128
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:8:

GCCAGTGATG CTAAAGGTTG TATTGCATAT ATACATATAT ATATATATAT ATATATATAT        60

ATATATATAT ATATATATAT ATATATATAT TTTAATTTGA TAGTATTGTG CATAGAGCCA       120

CGTATGTT                                                                128

( 2 ) INFORMATION FOR SEQ ID NO:9:

( i ) SEQUENCE CHARACTERISTICS:
        ( A ) LENGTH: 243
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:9:

TCCAGCCTCG GAGACAGAAT GAGACTCCAT CAAAAACAAG AAAGAAAGAA AGACAAAGAG        60

AGAAAGAAAG AAAGAAAGAA AGAAAGAAAG AGAGAGAGAG AGAGAGAGAG AGAAAGAAAG       120

AAAGAAAGAA AGAAAGAAAG AAAGAAAGAA AGAAAGAAAG AAAGAAAGAA GGAAAGAAAG       180

-continued

```
AAAGGAAACT  AAAATAACTA  AATAACTGAG  TAGCACCACA  CCACCTGCTC  TGGAGAAAGG       240
ACT                                                                          243
```